United States Patent [19]

Forward et al.

[11] 4,016,255
[45] Apr. 5, 1977

[54] ORAL HYGIENE COMPOSITIONS

[75] Inventors: Geoffrey Charles Forward, Redhill; Susan Ann Duke, Croydon, both of England

[73] Assignee: Beecham Group Limited, Great Britain

[22] Filed: Sept. 11, 1975

[21] Appl. No.: 612,285

[30] Foreign Application Priority Data

Sept. 28, 1974 United Kingdom ............ 42238/74

[52] U.S. Cl. .................................. 424/52; 424/54
[51] Int. Cl.² ...................... A61K 7/18; A61K 7/22
[58] Field of Search .................................. 424/52, 54

[56] References Cited

UNITED STATES PATENTS

| | | | |
|---|---|---|---|
| 2,542,518 | 2/1951 | Henschel | 424/54 |
| 2,542,886 | 2/1951 | Wach | 424/54 |
| 2,588,324 | 3/1952 | Lewis et al. | 424/54 |
| 2,588,992 | 3/1952 | Schlaeger | 424/54 |
| 2,601,238 | 6/1952 | Bell | 424/54 |
| 2,622,058 | 12/1952 | Kesel | 424/54 |
| 2,647,073 | 7/1953 | Singer | 424/54 |
| 3,227,618 | 1/1966 | Manahan et al. | 424/52 |
| 3,235,459 | 2/1966 | Francis | 424/52 |
| 3,277,118 | 12/1966 | Schmid et al. | 424/52 |
| 3,666,855 | 5/1972 | Muhler | 424/52 |

*Primary Examiner*—Shep K. Rose

[57] ABSTRACT

Oral hygiene anti-cariogenic compositions comprising a water-soluble fluoride compound and a potentiating amount of a water-soluble ammonium compound in molar ionic ratio ranges of 1.2:1 or greater, the ammonium compound not being a condensation product of ammonia and phosphorus pentoxide, the acid-solubility of dental enamel decreasing with increasing ammonium content.

15 Claims, No Drawings

ORAL HYGIENE COMPOSITIONS

This invention relates to oral hygiene compositions which reduce the acid-solubility of dental enamel.

We have observed that the activity of fluoride ions and fluorophosphate ions in reducing the acid-solubility of dental enamel is potentiated by the presence of ammonium ions. We have further observed that the potentiation effect increases with increasing ammonium ion concentration, and that particularly good results are achieved when the molar ratio of available fluoride (whether present as fluoride ion or as fluoride in bound form such as in fluorophosphate ions) is 1.2:1 or greater.

As far as we are aware, the prior art has not recognised this potentiation effect of ammonium ions and consequently there has previously been no reason to employ a high ammonium concentration in fluoride oral hygiene compositions. However, the prior art does indicate ammonium fluoride to be a preferred anticariogenic agent (here of course the molar ratio of ammonium:fluoride is 1:1). In addition, there are a number of proposals in the prior art to formulate together fluoride salts or other fluoride-containing substances and ammonium salts for use in anticariogenic mouthwashes, but in almost all cases of which we are aware, the molar ratio of ammonium:fluoride in previously proposed mouthwashes is either 1:1 or less than 1:1.

British Patent Specification No. 1,256,796 describes an oral composition such as a dentifrice, mouthwash or topical solution which comprises a carrier, (other than a common solvent) suitable for use in the oral cavity and an ammonium salt of a condensation product of ammonia and phosphorus pentoxide and optionally a fluoride-containing anticariogenic component. British Patent Specifications 1,260,332 and 1,260,333 also refer to fluoride-containing dental compositions containing an ammonium salt of a condensation product of ammonia and phosphorus pentoxide. In these three specifications, compositions are prepared containing a fluoride compound and the said ammonium salt wherein the theoretical molar ratio of ammonium ions to fluoride is greater than 1.2:1 (although it is not clear that in such compositions the molar ratio of available ammonium ion to available fluoride is greater than 1.2:1). However, these Specifications do not have as their object the potentiation of fluoride activity and this effect is not recognised anywhere in the Specifications.

Accordingly the present invention provides an oral hygiene composition comprising a physiologically acceptable water-soluble fluoride compound and a physiologically acceptable water-soluble ammonium compound, the molar ratio of available ammonium ion to available fluoride in said composition being 1.2:1 or greater, subject to the proviso that the ammonium compound is not an ammonium salt of a condensation product of ammonia and phosphorus pentoxide.

The water-soluble fluoride compound may be fully or only partially water soluble, and such compounds include, for example, sodium fluoride, potassium fluoride, ammonium fluoride, cuprous fluoride, zinc fluoride, stannous fluoride, sodium fluorosilicate, sodium fluorozirconate, sodium monofluorophosphate, aluminium mono- and di- fluorophosphate, fluorinated sodium calcium pyrophosphate, and fluorozirconate. Preferred fluoride compounds include sodium, potassium, ammonium and stannous fluorides and sodium monofluorophosphate. More than one fluoride compound may be employed, for example a mixture of sodium monofluorophosphate and sodium fluoride in amounts such that from 40 to 80% of the total fluoride content is provided by the sodium fluoride.

The water-soluble ammonium compound may be fully or only partially water soluble, and such compounds include ammonium chloride, ammonium bromide, ammonium sulphate, ammonium triphosphate, ammonium dihydrogen phosphate, or diammonium hydrogen phosphate. More than one ammonium compound may be employed, in which case ammonium fluoride and/or ammonium monofluorophosphate may be present.

The fluoride compound and the ammonium compound should be physiologically acceptable, and by this we mean physiologically acceptable at the concentration employed.

Since the fluoride theoretically present in the fluoride compound may not all be released into solution when the composition is in use (for example if the fluoride compound is only partly water-soluble or if other components of the composition combined with or otherwise neutralise some of the theoretical fluoride content), the amount of fluoride compound employed in the composition is determined by reference to the "available fluoride." By this term, we mean the proportion of the theoretical fluoride content of the composition which is available for uptake into the dental enamel.

Similarly, since the ammonium ion theoretically releasable by the ammonium compound may not all be released into solution when the composition is in use (for example if the ammonium compound is only partly water-soluble or if other components of the composition combine with a proportion of the ammonium ions to precipitate an insoluble ammonium compound), the amount of ammonium compound employed in the composition is determined by reference to the "available ammonium ion". By this term we mean the proportion of the theoretical ammonium content of the composition which is released into or is present in solution as free ammonium ion when the composition is used.

The molar ratio of available ammonium ion to available fluoride present in the composition is 1.2:1 or greater. The upper limit will generally not be greater than about 20:1. In general we have observed that the potentiation effect of ammonium ion on fluoride increases approximately logarithmically with linear increase in ammonium ion concentration.

The precise ratio chosen therefore depends mainly on factors dictated by compatability of the various ingredients of the composition, the physiological acceptability of the fluoride and ammonium compounds and the necessity to ensure that the taste of the composition is acceptable. Subject to compatability requirements, the molar ratio of available ammonium ion to available fluoride ion may range from 2:1 to 20:1, e.g. from 5:1 to 15:1, or more narrowly from 8:1 to 15:1. A particularly useful range which may be used is from 8:1 to 12:1, e.g. about 10:1.

The oral hygiene compositions of this invention may be presented as mouthwashes, toothpastes, chewing gums, dental creams, toothpowders and the like.

Typically, a mouthwash composition will contain from 10–1000, preferably 50–250 ppm of available fluoride, and a toothpaste will contain from 100–2500 e.g. from 750–1500, preferably about 1000 ppm of available fluoride.

In the case of a mouthwash, in addition to the fluoride compound and ammonium compound, other ingredients may be present providing these are compatible within the limits set by the preceding paragraphs. Thus antibacterial agents, vitamins, surfactants, flavourings, sweeteners, dyestuffs and antioxidants may also be present, with the balance of the composition being a liquid vehicle. Suitable vehicles include aqueous ethanol, aqueous isopropanol, aqueous n-propanol, aqueous sorbitol, aqueous glycerol, aqueous 1,2-propyleneglycol and aqueous 1,4-butanediol.

As is conventional, the mouthwash composition will usually be presented to the consumer in concentrated form, with instructions to dilute to the recommended concentration. In such cases, the relative proportions and absolute amounts of the fluoride compound and ammonium compound will be chosen with the recommended dilution in mind, i.e., the "available fluoride" and "available ion" are the amounts available at the recommended dilution.

In the case of a toothpaste, or toothpowder, again other ingredients than the fluoride compound and ammonium compound will almost certainly be present. These additional ingredients will usually be polishing agents, surfactants, gelling agents and humectants, and other excipients such as flavouring agents and colouring agents.

In choosing the polishing agent the compatability of the various ingredients of the toothpaste or toothpowder should be carefully considered. For example, if the ammonium compound is ammonium dihydrogen phosphate, the pH of a paste is important since above pH 8.0 ammonia is evolved and below pH 6.5 carbon dioxide would be evolved from calcium carbonate if present as a polishing agent. However, compatible systems can be found amongst the currently used polishing agents, and the possible fluoride and/or ammonium compounds.

Current polishing agents include water-soluble sodium or potassium metaphosphate, hydrated or anhydrous dicalcium phosphate, calcium pyrophosphate, silica in various forms such as silica xerogels, and silicates such as zirconium silicate, aluminium (trihydrate and anhydrous) calcium carbonate and polymeric materials such as acrylic polymers and cellulose, or mixtures thereof. The polishing agent is finely divided, generally with a particular size smaller than 10 microns, preferably between 2 and 6 microns. The polishing agent may be employed in an amount of from 10 to 99% by weight of the dentifrice, preferably 20–75% by weight; the higher percentages being more appropriate for tooth powders.

A suitable surfactant is normally included in dentifrice compositions, preferably this being a water-soluble non-soap or synthetic organic detergent. Suitable detergents are the water-soluble salts of: higher fatty acid monoglyceride monosulphates (for example sodium dodecylbenzenesulphonates): and higher alkyl sulphoacetates (for example sodium lauryl sulphoacetate). There may also be used the saturated higher aliphatic acyl amides of lower aliphatic amino carboxylic acids having 12 to 16 carbon atoms in the acyl radical and in which the acids have 2 to 6 carbon atoms, such as the fatty acid amides of glycine, sarcosine, alanine, 3-aminopropanoic acid and valine, particularly the N-lauroyl, myristoyl and palmitoyl sarcosinate compounds. Conventional nonionic surfactants may also be included if desired.

The surface-active materials are generally present in an amount of 0.05 to 10% preferably 0.5 to 5% by weight of the dentifrice composition.

In general the liquid base of toothpastes or dental cream will comprise chiefly water, glycerol, sorbitol or propylene glycol, including suitable mixtures thereof. It is advantageous usually to use a mixture of water and glycerine and synthetic gums and gum-like materials, preferably Irish Moss or sodium carboxymethylcellulose, may be used.

Other gums which may be used are gum tragacanth, hydroxyethyl cellulose, polyvinylpyrrolidone and starch. They are usually used in an amount up to 10%, preferably from pH 6 to pH 9, assuming compatability of ingredients at those pH's.

Other materials may be added such as soluble saccharin, flavouring oils, chloroform (e.g. oils of spearmint, peppermint, wintergreen), colouring or whitening agents, (e.g. titanium dioxide), preservative (e.g. sodium benzoate), emulsifying agents, acidifying agents (e.g. citric acid), silicones, alcohol, menthol and chlorophyll compounds (e.g. sodium copper chlorophyllin), and corrosion inhibitors such as sodium silicate etc.

Although the anti-caries effect of oral hygiene compositions containing high concentrations of ammonium and standard concentrations of fluoride compounds is clear and of undoubted benefit, difficulties can arise during the formulation of these components into typical oral compositions. In general, the most stable compositions will be mouthwashes. With toothpastes corrosion problems may require the use of lacquered aluminium tubes. In addition the reaction of the ammonium ion with certain thickening agents and the like may require an investigation to determine compatible ingredients. This, however, will be a routine investigation and stable formulation ingredients will normally be available.

The following tests demonstrate the potentiation effect of ammonium ions on fluoride activity:

EXPERIMENT 1

Discs of compressed hydroxyapatite (HA) (the mineral constituent of dental enamel) containing 10% by weight of polyethylene as binder, were briefly pretreated (1 minute) with the test solution, washed, and then placed below a rotating propellor in a dissolution cell containing molar acetate buffer pH 4.65. Each disc was then dissolved for 1 hour at 37° C, and the calcium dissolving from it was compared with that dissolving from a control-water-pretreated disc. Activity is expressed in terms of percentage reduction in solubility of the treated disc when compared with the solubility of the control.

RESULTS (Solution)

Discs were pretreated with sodium fluoride and sodium monofluorophosphate, and then with these salts with equimolar and excess amounts of ammonium salts added, the results are shown in Table I. Ammonium fluoride and ammonium monofluorophosphate were also tested.

TABLE I:

The effect of $NH_4^+$ ion on fluoride activity

| FLUORIDE SOURCE | Conc$^n$ | $NH_4^+$ SOURCE | Conc$^n$ | % reduction HA Solubility |
|---|---|---|---|---|
| Sodium Fluoride | $1\times10^{-3}$M | — | — | 36.4 |
| Sodium Fluoride | $1\times10^{-3}$M | $NH_4Cl$ | $1\times10^{-3}$M | 46.6 |
| Sodium Fluoride | $1\times10^{-3}$M | $NH_4Cl$ | $5\times10^{-3}$M | 58.3 |
| Ammonium Fluoride | $1\times10^{-3}$M | — | — | 46.6 |
| Sodium MFP | $1\times10^{-2}$M | — | — | 28.2 |
| Sodium MFP | $1\times10^{-2}$M | $NH_4Cl$ | $1\times10^{-2}$M | 38.6 |
| Ammonium MFP | $1\times10^{-2}$M | — | — | 39.4 |
| Sodium MFP | $1\times10^{-2}$ | $NH_4Cl$ | $5\times10^{-2}$M | 52.6 |

From these results it can be seen that equimolar amounts of ammonium:fluoride give a result equivalent to the ammonium/fluoride salt. Excess amounts of ammonium ions give increased activity.

Other ammonium salts were tested, ammonium sulphate, ammonium dihydrogen phosphate, and diammonium hydrogen phosphate were as effective as the chloride; some salts tended to complex fluoride because of the nature of their anions, and therefore their effectiveness was reduced in proportion to the degree of fluoride inactivation. In such cases by increasing the fluoride compound, activity could be improved.

To determine the effect of varying amounts of ammonium ions on the activity of fluoride, increased concentrations of ammonium dihydrogen phosphate were added to a mixture of sodium fluoride and sodium monofluorophosphate. The results are shown in Table II.

TABLE II

Reduction in hydroxyapatite disc solubility following one minute pretreatment with a NaF/MFP (250 ppm $F^-$ 3:2 ratio) Solution containing various ammonium ion concentrations

| Ammonium * Ion Concentration ppm in Fluoride Solution | % Reduction in HA Disc Solubility by Ca assay |
|---|---|
| — | 42% |
| 250 | 50% |
| 750 | 55% |
| 1250 | 58% |
| 2500 | 62% |
| 5000 | 64% |
| 9000 | 65% |

*As Ammonium Dihydrogen Phosphate pH of all solutions 6.5 – 7.0

These results show that the activity of the ammonium/fluoride mixtures increases approximately logarithmically with linear increases in ammonium ion concentration. Excess ammonium ions were again shown to give increased activity over equimolar mixtures.

EXPERIMENT 2

Effect of Ammonium Ion on the Fluoride — Dental Enamel Reaction

It is believed that dental enamel reacts with fluoride to give two products, calcium fluoride and "fluorapatite", and it is believed that it is only the formation of "fluorapatite" which has a cariostatic effect.

By measuring the total fluoride uptake by hydroxyapatite powder and also the amount of calcium fluoride formed after each fluoride treatment, the fluoride bound to hydroxyapatite can be estimated by subtraction. This fluoride-hydroxyapatite product is preferably referred to as 'fluoridated hydroxyapatite' (FHA) since there is no specific proof that it has the fluorapatite structure.

RESULT

| Treatment | Conc$^n$ | pH | Fluoride as FHA ppm |
|---|---|---|---|
| NaF | $1\times10^{-3}$ | 8.2 | 80 |
| $NH_4F$ | $1\times10^{-3}$ | 8.5 | 151 |
| NaF | $1\times10^{-3}$ | 7.1 | 70 |
| $NH_4F$ | $1\times10^{-3}$ | 7.2 | 151 |
| NaF | $1\times10^{-3}$ | 2.5 | 90 |
| $NH_4F$ | $1\times10^{-3}$ | 2.5 | 175 |

It can be seen the FHA is formed in greater quantities in the presence of $NH_4^+$ than with sodium fluoride over the pH range 2.5 to 8.5, and this might explain the potentiation effect of $NH_4^+$ on the anticariogenic effect of fluoride ions.

The following are examples of toothpaste formulations in accordance with the invention. It should be noted that high concentrations of ammonia sometimes give rise to corrosion problems in unlacquered aluminium tubes and hence the lacquered variety should be used in the following 2 examples:

|  | I | II |
|---|---|---|
| Glycerin | 25.00 | 25.00 |
| Sodium carboxymethylcellulose | 1.00 | 1.00 |
| Sodium saccharin | 0.20 | 0.20 |
| Sodium monofluorophosphate | 0.76 | 0.38 |
| Sodium fluoride | — | 0.11 |
| Ammonium dihydrogen phosphate | 1.92 | 1.61 |
| Diammonium hydrogen phosphate | — | 0.92 |
| Calcium carbonate | 45.00 | 45.00 |
| Sodium lauryl sulphate | 2.00 | 2.00 |
| Preservative | 0.20 | 0.20 |
| Flavour | 1.00 | 1.00 |
| Water | to 100% | to 100% |

We claim:

1. An oral hygiene composition comprising a physiologically acceptable water-soluble fluoride compound selected from sodium fluoride, potassium fluoride, ammonium fluoride, stannous fluoride, sodium monofluorophosphate and mixtures thereof and a physiologically acceptable water-soluble ammonium compound selected from ammonium chloride, ammonium bromide, ammonium sulfate, ammonium triphosphate, ammonium dihydrogen phosphate, diammonium hydrogen phospate and mixtures thereof, the molar ratio of available ammonium ion to available fluoride in said composition being 1.2:1 or greater.

2. A composition as claimed in claim 1 wherein the said fluoride compound is a mixture of sodium fluoride and sodium monofluorophosphate in amounts such that from 40 to 80% of the total fluoride content is provided by the sodium fluoride.

3. A composition as claimed in claim 1 which includes ammonium fluoride, ammonium monofluorophosphate or both.

4. A composition as claimed in claim 1 wherein the molar ratio of available ammonium ion to available fluoride is from 1.2:1 to 20:1.

5. A composition as claimed in claim 4 wherein said ratio is from 2:1 to 20:1.

6. A composition as claimed in claim 4 wherein said ratio is from 5:1 to 15:1.

7. A composition as claimed in claim 4 wherein said ratio is from 8:1 to 15:1.

8. A composition as claimed in claim 4 wherein said ratio is from 8:1 to 12:1.

9. A composition as claimed in claim 4 wherein said ratio is about 10:1.

10. A composition as claimed in claim 1 formulated as a mouthwash, toothpaste, dental cream, toothpowder or chewing gum.

11. A composition as claimed in claim 1 formulated as a mouthwash containing from 10 to 1000 ppm of available fluoride.

12. A mouthwash as claimed in claim 11 containing from 50 to 250 ppm of available fluoride.

13. A composition as claimed in claim 1 formulated as a toothpaste containing from 100 to 2500 ppm of available fluoride.

14. A toothpaste as claimed in claim 13 containing from 750 to 1,500 ppm of available fluoride.

15. A toothpaste as claimed in claim 13 containing about 1000 ppm of available fluoride.

* * * * *